United States Patent [19]
Goodchild

[11] Patent Number: 5,612,469
[45] Date of Patent: Mar. 18, 1997

[54] ENHANCEMENT OF RIBOZYME CATALYTIC ACTIVITY BY A NEIGHBORING FACILITATOR OLIGONUCLEOTIDE

[75] Inventor: John Goodchild, Worcester, Mass.

[73] Assignee: Worcester Foundation for Experimental Biology, Worcester, Mass.

[21] Appl. No.: 431,625

[22] Filed: May 1, 1995

Related U.S. Application Data

[63] Continuation of Ser. No. 138,896, Oct. 19, 1993, abandoned, which is a continuation of Ser. No. 830,713, Feb. 4, 1992, abandoned.

[51] Int. Cl.$^6$ .............................. C12N 15/11; C12Q 1/68
[52] U.S. Cl. ..................... 536/23.1; 536/232; 536/245; 435/6; 435/91.1; 435/91.31; 435/172.1
[58] Field of Search ..................... 435/6, 91.3, 91.31, 435/91.1, 172.1, 172.3, 91.51; 536/24.5, 24.1, 23.1, 23.2

[56] References Cited

FOREIGN PATENT DOCUMENTS

0421376A1  4/1991  European Pat. Off. .

OTHER PUBLICATIONS

Uhlmann et al. Chemical Reviews 90:544–575 (1990).
Sarven et al. Science 247:1222 (1990).
Rossi et al. J. Cell. Biochem. Suppl. 14A, D428 (1990).
Muesing et al Nature 313:450 (1985).
Haseloff et al (1988) Nature 334, 585–591.
Hortsch el al (1990) Develop. 110, 1327–1340.
McCormack et al (1990) Proced. Nat. Acad. Sci. 87, 5227–5231.
Burch et al (1991) J. Clin. Invest. 88, 1190–1196.
Hampel and Tritz, Biochem. 28: 4929–4933 (1989), "RNA Catalytic Properties of the Minimum (–)sTRSV Sequence.".
Hampel et al., Nuc. Acids. Res. 18: 299–304 (1990), "'Hairpin' catalytic RNA model: evidence for helices and sequence requirements for substrate RNA.".
Fedor and Uhlenbeck, Proc. Natl. Acad. Sci. USA 87: 1668–1672 (1990), "Substrate Sequence Effects on hammerhead RNA catalytic efficiency.".

Koizumi et al., FEBS 239: 285–288 (1988), "Cleavage of specific sites of RNA by designed ribozymes.".
Lehman and Joyce, Nature 361: 182–185 (1993), "Evolution in vitro of an RNA enzyme with altered metal dependence.".
Goodchild et al., Arch. Biochem. and Biophys. 263: 401–409 (1988), "Inhibition of Rabbit β–Globin Synthesis by Complementary Oligonucleotides: Identification of mRNA Sites Sensitive to Inhibition".
Uhlenbeck, Nature 328: 596–600 (1987), "A small catalytic oligoribonucleotide".
Kutyavin, et al., 1988, FEBS 238: 35–38, "N–2–Hydroxyethyl)phenazinium derivatives of oligonucleotides as effectors of the sequence–specific modification of nucleic acids with reactive oligonucleotide derivatives".
Maher and Dolnick, 1988, Nucleic Acids Res. 16: 3341–3358, "Comparative hybrid arrest by tandem antisense oligodeoxyribonucleotides or oligodeoxyribonucleoside methylphosphonates in a cell–free system".
Goodchild and Kohli, 1991, Archives of Biochem. & Biophysics 284: 386–391, "Ribozymes that cleave an RNA sequence from human immunodeficiency virus: the effect of flanking sequence on rate".
Sproat, et al., 1990, Nucleic Acids Res. 18:41–49, "New synthetic routes to protected purine 2'–O–methylriboside–3'–O–phosphoramidites using a novel alkylation procedure".
Goodchild, J., 1992, Nucleic Acids Res. 20: 4607–4612, "Enhancement of ribozyme catalytic activity by a contiguous oligodeoxynucleotide (facilitator) and by 2–'O–methylation".

*Primary Examiner*—John L. LeGuyader
*Attorney, Agent, or Firm*—Banner & Witcoff, Ltd.

[57] ABSTRACT

Methods are disclosed for increasing ribozyme catalytic activity without reducing specificity, which methods comprise contacting an RNA molecule with a ribozyme and a facilitator oligonucleotide.

The present invention further provides compositions comprising a ribozyme and an effective amount of a facilitator oligonucleotide.

9 Claims, 3 Drawing Sheets

ENHANCEMENT OF RIBOZYME CATALYTIC ACTIVITY BY A NEIGHBORING FACILITATOR OLIGONUCLEOTIDE

This application is a continuation application of Ser. No. 08/138,896, filed on Oct. 19, 1993, now abandoned, which is a continuation of application Ser. No. 07/830,713, filed Feb. 4, 1992, now abandoned.

BACKGROUND OF THE INVENTION

1. Field of the Invention

This invention relates to ribozymes that cleave RNA, and more specifically to the enhancement of ribozyme catalytic activity using a facilitator oligonucleotide complementary to an RNA sequence contiguous to the ribozyme.

2. Description of the Related Art

Drugs might be based on RNA catalysts (ribozymes) designed to cleave viral or messenger RNA with high specificity at a rapid rate. These requirements historically have been mutually limiting.

Ribozymes consist of a catalytic core having flanking sequences adjacent the core which hybridize to the substrate RNA. The simplest catalytic core is an RNA motif known as a hammerhead.

Ribozyme specificity depends on the number of base pairs formed between the ribozyme flanking sequences and its RNA substrate. Increased base pairing has been shown to decrease the rate of cleavage. Goodchild and Kohli, Arch. Biochem. Biophys., 284: 386–391 (1991). Goodchild and Kohli studied the cleavage of a sequence from HIV-1RNA by various hammerhead ribozymes and determined that the rate of cleavage was dependent on the length of the flanking sequence. Shorter sequences were shown to result in weaker binding between the ribozyme and the cleavage products together with increased rate of cleavage. A ribozyme with 12 flanking sequences cleaved 10 times faster then one with 20 bases.

However, to have the requisite selectivity or specifity, i.e., the ability to discriminate between all RNA molecules in a cell, a ribozyme must form a minimum of about 15 base pairs with the target substrate. This requirement for selectivity limits the rate of cleavage that may be realized.

Accordingly, ribozymes having increased catalytic activity or methods of increasing ribozyme catalytic activity are needed.

Koizumi et al., FEBS Lett. 239: 285–288 (1988), discuss the design of two ribozymes for site-specific cleavage of RNA. A UA site in an undecaribonucleotide was cleaved by a ribozyme consisting of two partially paired oilgoribonucleotides with chain lengths of 19 and 15. The other ribozyme, which consists of 19-mer and a 13-mer, recognized a UC sequence at positions 42 and 43 of 5 S rRNA.

Haseloff and Gerlach, Nature 334: 585–59 (1988), discuss the dissection of the RNA substrate and enzyme activities from a single self-cleaving domain from the (+) strand of the satellite RNA of tobacco ringspot virus (sTobRV). Inspection of the separated substrate and ribozyme activities, in comparison with other naturally-occurring self-cleaving domains, led to a model for the design of oligoribonucleotides which posses new and highly sequence-specific endoribonuclease activities. This model was successfully tested by the design and construction of ribozymes targeted against three sites within the Tn9 chloramphenicol acetyltransferase (CAT) messenger RNA sequence.

Hampel and Tritz, Biochemistry 28: 4929–4933 (1989), identified an RNA catalytic domain within the sequence of the 359 base long negative-strand satellite RNA of tobacco ringspot virus. The catalytic domain contains two minimal sequences of RNA, a 50 base catalytic RNA sequence, and a 14 base substrate RNA sequence. The catalytic complex of catalytic RNA/substrate RNA represents a structure not previously found in any RNA catalytic reaction.

Hampel et al., Nucleic Acids Res. 18: 299–304 (1990) discuss the identification of the catalytic domain within the sequence of the negative strand of the satellite RNA of tobacco ringspot virus. Minimum energy RNA folding calculations predict a two dimensional model with four major helical regions which are supported by mutagenesis experiments. This model for the catalytic complex consists of a 50 base catalytic RNA and a 14 base substrate RNA folded together in a type of hairpin two dimensional structure. Part of the recognition region between the catalyst and substrate is two helices of 6 bases and 4 bases respectively. Catalytic activity remains when the bases in these two helices are changed but base pairing is maintained. Thus an appropriately engineered 'hairpin' catalyst is capable of cleaving heterologous RNA.

Uhlenbeck, Nature, 328: 596–600 (1987) describes the synthesis of two oligoribonucleotides that can combine to form a structure consistent with the consensus self-cleaving domain. Because rapid cleavage of one of the oligomers was observed only when the other was present, the domain was necessary and sufficient for cleavage. The properties of the cleavage reaction were studied in detail. Nearly complete cleavage occurred even with large excess of the oligomer that was cleaved. This indicates that the oligomer that is uncleaved can cycle in the reaction and therefore be considered to act as a catalyst in the cleavage of the other oligomer.

Fedor and Uhlenbeck, Proc. Natl. Acad. Sci. USA 87: 1668–1672 (1990), analyzed the kinetics of cleavage for several hammerhead sequences to characterize the reaction mechanism and explore how nucleotides involved in substrate binding affect cleavage.

Goodchild et al., Arch. Biochem. Biophys. 263: 401–409 (1988) discusses the effects of a series of synthetic oligonucleotides (hybridons) complementary to the 5' non-coding regions of rabbit β-globin mRNA on endogenous protein synthesis in a rabbit reticulocyte cell-free translation system. With highly purified hybridons inhibition was completely specific for beta globin. Mixtures of two oligonucleotides binding contiguously to the mRNA were more effective than either oligomer alone.

Maher and Dolnick, Nucleic Acids Res. 16: 3341–3358 (1988) report that antisense oligonucleotides containing either anionic diester or neutral methylphosphonate internucleoside linkages were prepared by automated synthesis, and subsequently compared for their ability to arrest translation of human dihydrofolate reductase (DHFR) mRNA in a nuclease treated rabbit reticulocyte lysate. In the case of oligodeoxyribonucleotides, tandem targeting of three 14-mers resulted in synergistic and complete selective inhibition of DHFR synthesis at a total oligomer concentration of 25 µM.

Kutyavin et al, FEBS Lett. 238: 35–38 (1988) report that mono- and diphenazinium derivatives of oligonucleotides complementary to the DNA sequence adjacent to the target sequence of the addressed alkylation of DNA significantly enhance the extent and specificity of alkylation by p-(N-2-chloroethyl-N-methylamino(benzylamido) derivatives of the addressing oligonucleotides.

SUMMARY OF THE INVENTION

The present invention provides methods for increasing ribozyme catalytic activity without reducing specificity, which methods comprise contacting an RNA molecule with a ribozyme and a facilitator oligonucleotide.

The present invention further provides compositions comprising a ribozyme and an effective amount of a facilitator oligonucleotide.

DETAILED DESCRIPTION OF THE INVENTION

Figure 1:
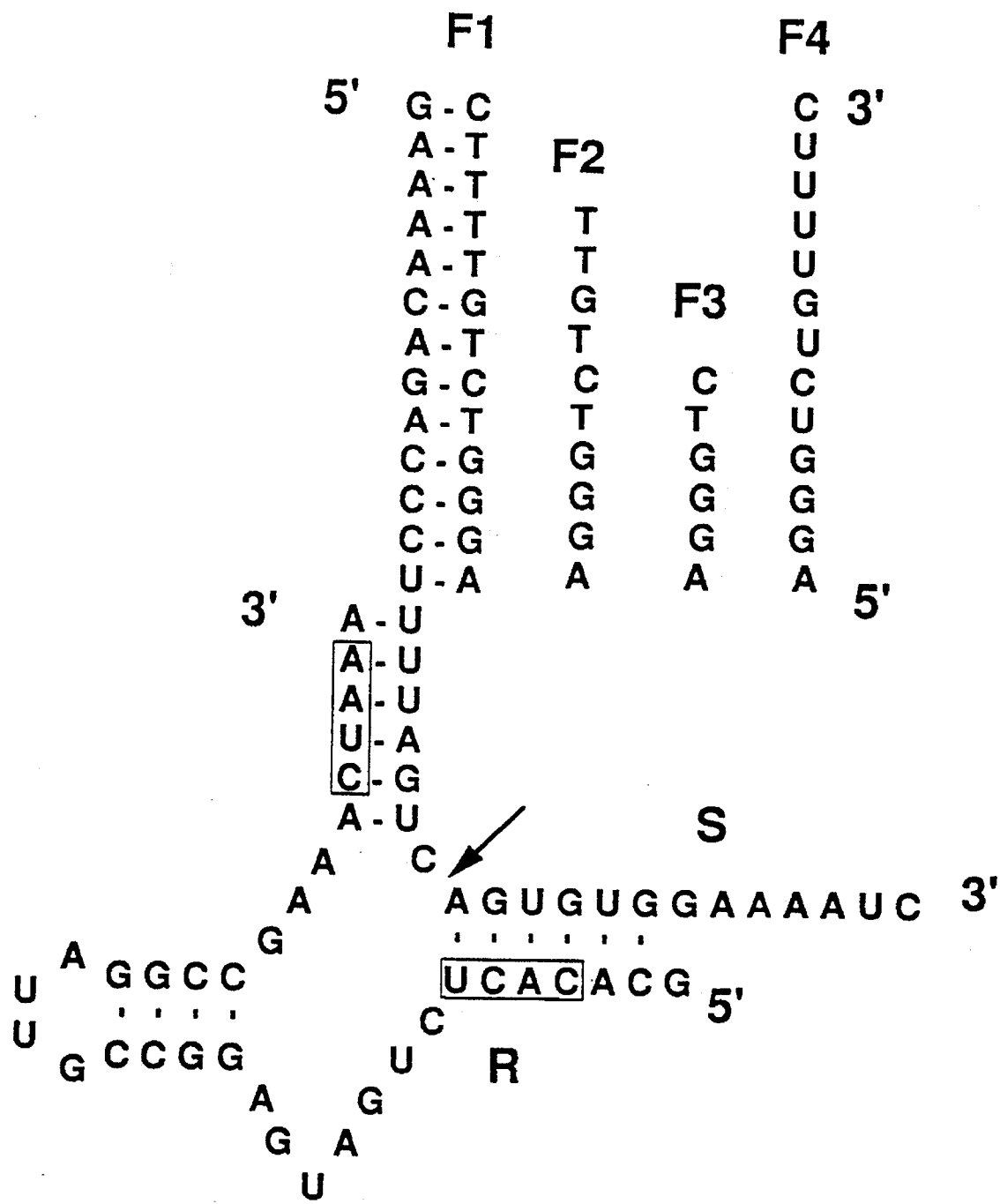
FIG. 1 shows the nucleotide sequences of substrate RNA (S), ribozyme (R) and facilitator oligodeoxynucleotides $F_1$, $F_2$, $F_3$, and facilitator ribooligonucleotide $F_4$ with the same sequence as $F_1$. The site of cleavage of substrate is indicated by the arrow.

The development of antiviral drugs based on RNA catalysts has been inhibited by the mutually limiting requirements of high specificity and RNA cleavage rate. Increased base pairing between a ribozyme and a substrate RNA has been shown to decrease the rate of RNA cleavage. In order for a ribozyme to discriminate between all RNAs in a cell, a ribozyme must form about 15 base pairs with the target. However, longer flanking sequences in ribozymes is related to decreased catalytic cleavage.

It has been unexpectedly discovered that rate of cleavage of substrate RNA by a ribozyme is enhanced by introducing an oligonucleotide into the system which hybridizes immediately adjacent to the ribozyme. The facilitator oligonucleotides of the present invention are designed to bind to RNA sequences contiguous to flanking sequences of the ribozymes.

The facilitator oligonucleotides suitable for use in the instant invention may be either deoxyoligonucleotides or ribo-oligonucleotides. Furthermore, the facilitator oligonucleotide may be selected to bind to a sequence contiguous to the flanking sequence either at the 5' or the 3' side of the ribozyme. In addition, a combination of two facilitator oligonucleotides may be employed, where one facilitator is bound contiguously to the 3' flanking sequence and the other to the 5' flanking sequence. Alternatively, a plurality of facilitators may be employed to catalyze ribozyme activity. For example, in a system employing three facilitators, two facilitators could bind contiguously to the 3' flanking sequence, while a single additional facilitator could bind contiguously to the 5' flanking sequence. A variety of other combinations are possible.

The facilitator oligonucleotides of the present invention typically comprise between about 5 and 50 nucleotides. More preferred facilitator oligonucleotides comprise between about 5 and 15 nucleotides. Particularly preferred facilitators according to the invention comprise about 13 nucleotides. Selection of a facilitator of a specific length is related to the length of the ribozyme flanking sequences.

In addition, facilitator deoxynucleotides may be selected to have between about 5 and 50 nucleotides complementary to the RNA substrate sequence as well as additional nucleotides which are not complementary to the RNA sequence.

The specific facilitator oligonucleotides are synthesized to bind to the desired RNA sequences such that they are contiguous to the flanking sequences of various ribozymes that cleave related RNA sequences. As described here, the oligonucleotides can be synthesized on automated DNA synthesizers or from DNA templates.

The facilitator oligonucleotides may be synthesized such that they are not completely contiguous to the flanking sequence of the desired ribozyme. For example, the facilitator may be synthesized such that, when the ribozyme and facilitator oligonucleotide are bound to the substrate RNA, a small gap of from one to about five oligonucleotides exists between the ribozyme and the facilitator oligonucleotide.

The facilitator oligonucleotides may be synthesized and subsequently modified to include moieties which will influence the rate of substrate cleavage by ribozyme, increase uptake by cells, or increase resistance to degradation.

By increasing the number of bases of the substrate RNA bound near the cleavage site, facilitators permit use of faster acting ribozymes with shorter flanking sequences. In viral applications, facilitators might be of dual benefit in also directing cleavage of the viral RNA by endogenous ribonuclease H.

The present invention also includes compositions which comprise a ribozyme and an effective amount of a facilitator oligonucleotide. In any treatment, however, the compositions comprising the ribozyme and facilitator oligonucleotide must be administered to individuals in a manner capable of delivering the oligonucleotide and ribozyme initially into the blood stream and subsequently into cells.

The compositions of the invention may be administered parenterally, orally, by inhalation or spray or rectally in dosage unit formulations containing conventional non-toxic pharmaceutically acceptable carriers, adjuvants and vehicles. The term "parenteral" as used herein includes subcutaneous injections, intravenous, intramuscular, intrasternal injection or infusion techniques. The compositions of the invention would be provided in a pharmaceutical formulation comprising the composition and a pharmaceutically acceptable carrier. In order for the compositions to be suitable for oral administration, oligonucleotides and ribozymes must be resistant to nucleases. Such resistance to nucleases may be imparted to the oligonucleotides and ribozymes by, for example, internucleotide phosphate modifications. Modified internucleotide phosphates suitable for use in the facilitator oligonucleotides of the present invention include phosphorothioates, methylphosphonates, phosphoramidates, and phosphotriesters.

The amount of active composition that may be combined with the carrier materials to produce a single dosage form will vary depending upon the host treated and the particular mode of administration. It will be understood that the specific dose level for any particular patient will depend upon a variety of factors including the activity of the specific composition employed, the age, body weight, general health, sex, diet, time of administration, route of administration, severity of the particular disease undergoing therapy.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

1. Preparation of RNA Substrate

A synthetic RNA substrate strand (S) was prepared to correspond to the sequence 146–173 in HIV-1 RNA. This RNA substrate strand was transcribed from synthetic DNA templates following a method described by Milligan and Uhlenbeck, Nucleic Acids Res. 15: 8783–8798 (1987), in a reaction containing Tris-HCl (40mM, pH 8.1), $MgCl_2$ (6 mM), spermidine (1 mM), dithiothreitol (50 mM), bovine serum albumin (50 µg per ml), inorganic pyrophosphatase (4 units per ml), T7 RNA polymerase (4000 units per ml) and four ribonucleotide 5'-triphosphates (1 µM each) supplemented with $\alpha\text{-}^{32}P$-UTP (3000 Ci/mmol). After incubation at 37° C. for 2 hours, the RNA was purified by electrophoresis in 10% polyacrylamide gels containing 8M urea. The radiolabeled RNA was quantitated using the specific activity of the incorporated $^{32}P$.

2. Preparation of Hammerhead Ribozyme

A hammerhead ribozyme (R) designed to cleave RNA substrate strand S was prepared. The hammerhead ribozyme was prepared by automated chemical synthesis using standard phosphoramidite reagents. Products were purified by electrophoresis in 15% polyacrylamide gels containing 8M urea, eluted by crush and soak in 0.5M ammonium acetate, desalted and quantitated by UV absorption.

3. Preparation of Facilitator and Control Oligonucleotides

Facilitator oligonucleotides $F_1$, $F_2$, and $F_3$ were prepared to contain 13, 10, and 6 nucleotides respectively, and to hybridize to substrate S contiguously with ribozyme R. Facilitator oligoribonucleotide $F_4$ was prepared with the same sequence as $F_1$. In addition, a control oligonucleotide having a random sequence was synthesized. The sequences of the facilitator oligonucleotides are shown in FIG. 1.

Both ribo- and deoxyoligonucleotides were prepared by automated chemical synthesis utilizing essentially the same procedures set forth in part 2 of this Example.

EXAMPLE 2

Cleavage of Substrate RNA

The cleavage of substrate RNA by ribozyme R was studied both with and without facilitator oligo $F_1$. The cleavage of substrate RNA gave products $P_1$ and $P_2$ having chain lengths expected from cleavage at the site indicated in FIG. 1.

Figure 2:
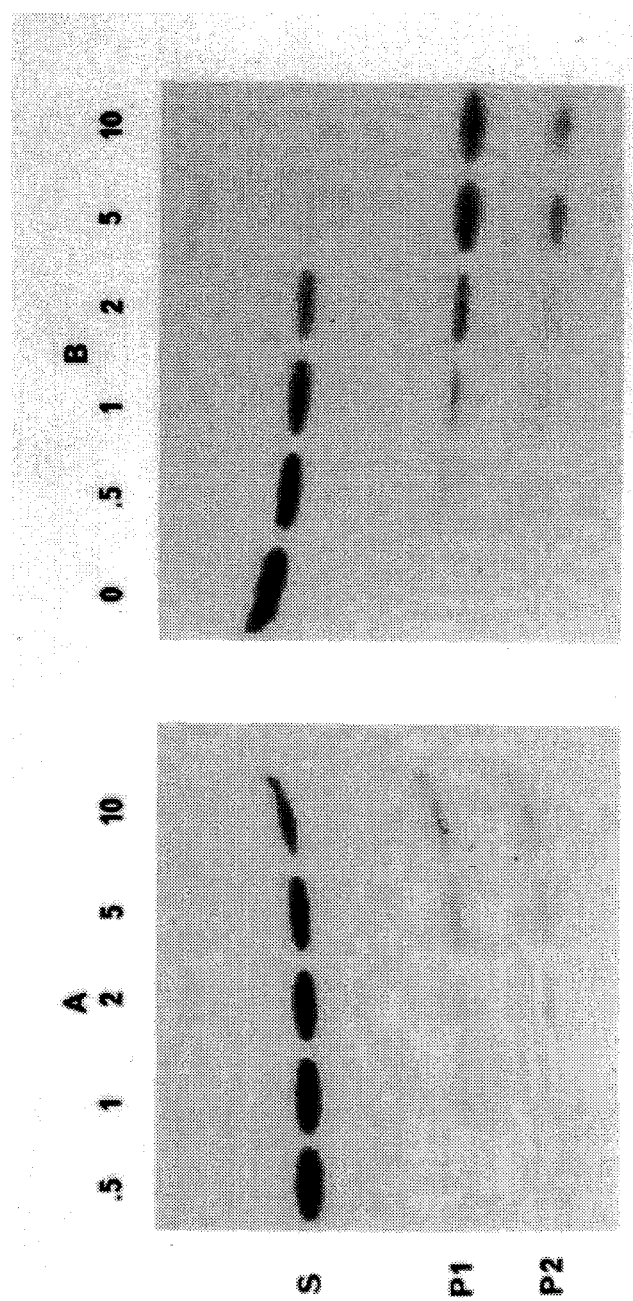
FIG. 2A is an autoradiograph showing the results of cleavage of radiolabelled substrate S by ribozyme R without facilitator oligonucleotide to give products $P_1$ and $P_2$ containing 20 and 13 nucleotides respectively.
FIG. 2B is an autoradiograph showing the results of cleavage of radiolabelled substrate S by ribozyme R in the presence of facilitator oligonucleotide $F_1$ to give products $P_1$ and $P_2$ containing 20 and 13 nucleotides respectively.

The cleavage reactions were run as follows: a solution (45 µl) containing substrate (13.4 µM), ribozyme (0.67 µM) and facilitator where appropriate (20 µM) in 50 mMTris.HCl (pH 7.4) was brought to 37° C. Reaction was initiated by the addition of $MgCl_2$ (5 µL, 200 mM). After times of 0.5, 1, 2, 5, and 10 minutes, aliquots of 5 µL were added to 15 µl of saturated urea:200 mM EDTA (1:1) and cooled to about −70° C. with dry ice to stop the reaction. The samples were then denatured by heating in formamide loading buffer at 90° C. for 3 minutes and subsequently analyzed alongside molecular weight markers by electrophoresis in 15% polyacrylamide gel containing 7M urea. The products were autoradiographed. The autoradiographs are shown in FIG. 2. Panel A shows the results of the cleavage reaction without any facilitator oligonucleotide and Panel B shows the results of cleavage of facilitator oligo $F_1$.

EXAMPLE 3

Relation of Facilitator Length to Ribozyme Activity

Figure 3:
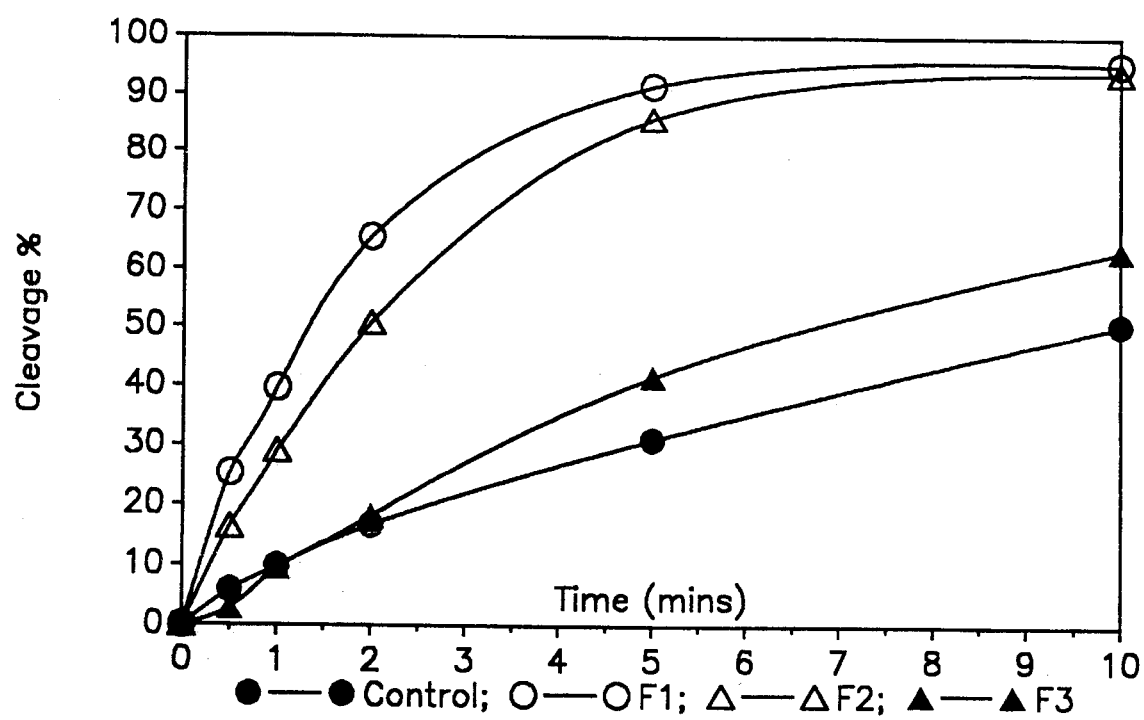
FIG. 3 is a graph of the time courses of cleavage reactions using facilitator oligonucleotides $F_1$, $F_2$, and $F_3$ and a control reaction with no facilitator oligonucleotide.

Cleavage of substrate RNA by ribozyme R was determined in the presence of facilitator oligonucleotides ($F_1$, $F_2$, $F_3$, and $F_4$) of varying length. Cleavage reactions were run under conditions substantially similar to those employed in Example 2 above. Products and starting materials were quantitated for each time point. Autoradiograph gels were sliced and the materials on the slices quantitated by scintillation counting. The results of this experiment are graphically shown in FIG. 3.

Cleavage with no facilitator reached about 94% completion after about 160 minutes. The facilitator of 13 deoxynucleotides significantly reduced reaction half life. Table 1 shows the time required for ribozyme to cleave 10 equivalents of substrate at 37° C. The longest facilitator, $F_1$, produced this half life time from 10 minutes to 1.3 minutes. The effects of facilitators $F_1$–$F_3$ were inversely related to their lengths. A control oligonucleotide of the same length as $F_1$ had no effect on the rate.

In a separate experiment, it was found that oligodeoxynucleotide $F_1$ was more effective at catalyzing ribozyme activity than oligoribonucleotide $F_4$ having the same sequence.

TABLE 1

| Half-Lives of Substrate in the Presence of Ribozyme and Facilitators | | |
|---|---|---|
| Facilitator | $[S]_o$[1] | Half-Life (min) |
| none | 2.7 | 10 |
| F1 | 2.7 | 1.3 |
| F2 | 2.7 | 1.9 |
| F3 | 2.7 | 6.9 |
| none | 0.9 | 40 |
| F1 | 0.9 | 4.9 |
| F4 | 0.9 | 12.3 |

[1]Starting concentrations of substrate (µM)

From the foregoing, it will appreciated that although specific embodiments of the invention have been described herein for purposes of illustration, various modifications may be made without deviating from the spirit or scope of the invention.

What is claimed is:

1. A composition comprising a ribozyme and an effective amount of a facilitator oligonucleotide.

2. The composition according to claim 1, wherein the facilitator oligonucleotide hybridizes with a sequence in the target RNA that is spaced no more than about three nucleotides from the target RNA to which the ribozyme hybridizes.

3. The composition according to claim 2, wherein the facilitator oligonucleotide comprises from about 5 to about 50 nucleotides.

4. The composition according to claim 3, wherein the facilitator oligonucleotide comprises from about 5 to about 15 nucleotides.

5. The composition according to claim 1, wherein the facilitator oligonucleotide comprises a modified internucleotide phosphate.

6. The composition according to claim 5, wherein the modified internucleotide phosphate comprises a phosphorothioate, methylphosphonate, phosphoramidate, or phosphotriester.

7. A facilitator oligonucleotide consisting of the sequence AGGGTC that binds to a sequence in a target RNA that is contiguous to a sequence in the target RNA to which a ribozyme hybridizes.

8. A facilitator oligonucleotide consisting of the sequence AGGGTCTGTT that binds to a sequence in a target RNA that is contiguous to a sequence in the target RNA to which a ribozyme hybridizes.

9. A facilitator oligonucleotide consisting of the sequence AGGTCTGTTTTC that binds to a sequence in a target RNA that is contiguous to a sequence in the target RNA to which a ribozyme hybridizes.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: RNA (genomic)

( i x ) FEATURE:
    ( A ) NAME/KEY: misc_RNA
    ( B ) LOCATION: 1..10
    ( D ) OTHER INFORMATION: /function="Ribozyme Facilitator"

( x i ) SEQUENCE DESCRIPTION: SEQ ID NO:1:

AGGGTCTGTT                                                                              10

( 2 ) INFORMATION FOR SEQ ID NO:2:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: RNA (genomic)

( i x ) FEATURE:
    ( A ) NAME/KEY: misc_RNA
    ( B ) LOCATION: 1..12
    ( D ) OTHER INFORMATION: /function="Ribozyme Facilitator"

( x i ) SEQUENCE DESCRIPTION: SEQ ID NO:2:

AGGTCTGTTT TC                                                                           12